(12) United States Patent
Ramsaroop et al.

(10) Patent No.: US 11,579,069 B2
(45) Date of Patent: Feb. 14, 2023

(54) METHODS AND SYSTEMS FOR INCREASING THE CAPACITY OF FLOW CYTOMETER BACTERIA DETECTION AND ANTIBIOTIC SUSCEPTIBILITY TESTING SYSTEMS

(71) Applicant: Renascent Diagnostics, LLC, Burlington, VT (US)

(72) Inventors: Shawn A. Ramsaroop, St. Louis, MO (US); Matthew D. Gombrich, Underhill, VT (US)

(73) Assignee: Renascent Diagnostics, LLC, Burlington, VT (US)

(*) Notice: Subject to any disclaimer, the term of this patent is extended or adjusted under 35 U.S.C. 154(b) by 412 days.

(21) Appl. No.: 16/779,405

(22) Filed: Jan. 31, 2020

(65) Prior Publication Data

US 2020/0249144 A1    Aug. 6, 2020

Related U.S. Application Data

(60) Provisional application No. 62/799,488, filed on Jan. 31, 2019.

(51) Int. Cl.
| | |
|---|---|
| *G01N 15/14* | (2006.01) |
| *G01N 35/00* | (2006.01) |
| *G01N 33/493* | (2006.01) |
| *G01N 33/49* | (2006.01) |
| *C12M 1/36* | (2006.01) |
| *G01N 15/10* | (2006.01) |
| *C12Q 3/00* | (2006.01) |

(52) U.S. Cl.
CPC ............ *G01N 15/1425* (2013.01); *C12M 1/36* (2013.01); *C12M 41/48* (2013.01); *C12Q 3/00* (2013.01); *G01N 33/49* (2013.01); *G01N 33/493* (2013.01); *G01N 35/0092* (2013.01); *G01N 15/1459* (2013.01); *G01N 2015/1006* (2013.01); *G01N 2035/0094* (2013.01)

(58) Field of Classification Search
CPC .. G01N 15/1425; G01N 33/49; G01N 33/493; G01N 35/0092; G01N 15/1459; G01N 2015/1006; G01N 2035/0094; G01N 2035/00356; C12M 1/36; C12M 41/48; C12Q 3/00; C12Q 1/18
See application file for complete search history.

(56) References Cited

U.S. PATENT DOCUMENTS

2018/0372697 A1 * 12/2018  DeWitte ................. G01N 30/88

FOREIGN PATENT DOCUMENTS

| EP | 2348301 A1 * | 7/2011 | ............. G01N 15/14 |
| WO | WO-2017189632 A1 * | 11/2017 | ............... C12Q 1/06 |

* cited by examiner

Primary Examiner — Jill A Warden
Assistant Examiner — Henry H Nguyen
(74) *Attorney, Agent, or Firm* — Caldwell Intellectual Property Law

(57) ABSTRACT

Aspects of the present disclosure include methods and systems for automated analysis of clinical fluid samples, such as urine, blood, or cerebral spinal fluid, where the number of fluid samples in increased or optimized without negatively impacting the accuracy of the analysis of a given fluid sample.

11 Claims, 6 Drawing Sheets

METHODS AND SYSTEMS FOR INCREASING THE CAPACITY OF FLOW CYTOMETER BACTERIA DETECTION AND ANTIBIOTIC SUSCEPTIBILITY TESTING SYSTEMS

RELATED APPLICATION DATA

This application claims the benefit of priority of U.S. Provisional Patent Application Ser. No. 62/799,488, filed Jan. 31, 2019, and titled "Methods And Systems For Increasing The Capacity Of Flow Cytometer Bacteria Detection And Antibiotic Susceptibility Testing Systems," which is incorporated by reference herein in its entirety.

FIELD OF THE INVENTION

The present invention generally relates to the field of flow cytometer bacteria detection and antibiotic susceptibility testing systems. In particular, the present invention is directed to methods and systems for increasing the capacity of flow cytometer bacteria detection and antibiotic susceptibility testing systems.

BACKGROUND

Flow cytometer and fluid handling systems may be used for performing quantitative analyses of fluids, such as urine, blood, or cerebral spinal fluid. Any of a variety of quantitative analyses may be performed, such as detection and enumeration of one or more events of interest in a fluid sample, such as detection and enumeration of bacteria populations in a fluid sample, as well as determination of the detected bacteria population's susceptibility to one or more antibiotics. Examples of such systems and methods are disclosed in international patent application number PCT/US2017/029492, filed on Apr. 25, 2017, and titled, "Systems, Devices And Methods For Sequential Analysis Of Complex Matrix Samples For High Confidence Bacterial Detection And Drug Susceptibility Prediction Using A Flow Cytometer," which is incorporated by reference herein in its entirety. Such automated systems can analyze a plurality of clinical samples, where the process for each sample includes a series of steps. While it is desirable to increase system throughput to maximize the number of clinical samples analyzed over a given time period, certain time periods during the analysis of a given sample, such as incubation time periods, are critical such that the system must be available to analyze a given sample at the end of such critical time periods.

SUMMARY OF THE DISCLOSURE

In one implementation, the present disclosure is directed to a method of sequencing an analysis of multi-well cassettes each containing a plurality of fluid samples. The method includes receiving pre-incubation analysis results for a first multi-well cassette containing a first plurality of fluid samples, wherein the pre-incubation analysis results indicate a number of the first plurality of fluid samples that contain a concentration of live bacteria above a threshold value; determining, according to the pre-incubation analysis results, a duration of time for performing a post-incubation analysis of one or more of the first plurality of fluid samples with a flow cytometer; and determining at least one of a start time for a pre-incubation analysis of a second multi-well cassette with the flow cytometer, or a start time of an incubation period for an incubation period for the second multi-well cassette, according to the determined duration of time for performing the post-incubation analysis.

In another implementation, the present disclosure is directed to a non-transitory machine-readable storage medium containing machine-readable instructions configured to cause a processor of a flow cytometer and fluid handling system to perform operations that include receiving pre-incubation analysis results for a first multi-well cassette containing a first plurality of fluid samples, wherein the pre-incubation analysis results indicate a number of the first plurality of fluid samples that contain a concentration of live bacteria above a threshold value; determining, according to the pre-incubation analysis results, a duration of time for performing a post-incubation analysis of one or more of the first plurality of fluid samples with a flow cytometer; and determining at least one of a start time for a pre-incubation analysis of a second multi-well cassette with the flow cytometer, or a start time of an incubation period for the second multi-well cassette, according to the determined duration of time for performing the post-incubation analysis.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Aspects of the present disclosure include methods and systems for automated analysis of clinical fluid samples, such as urine, blood, or cerebral spinal fluid, where the number of fluid samples is increased or optimized without negatively impacting the accuracy of the analysis of a given fluid sample.

Figure 1:
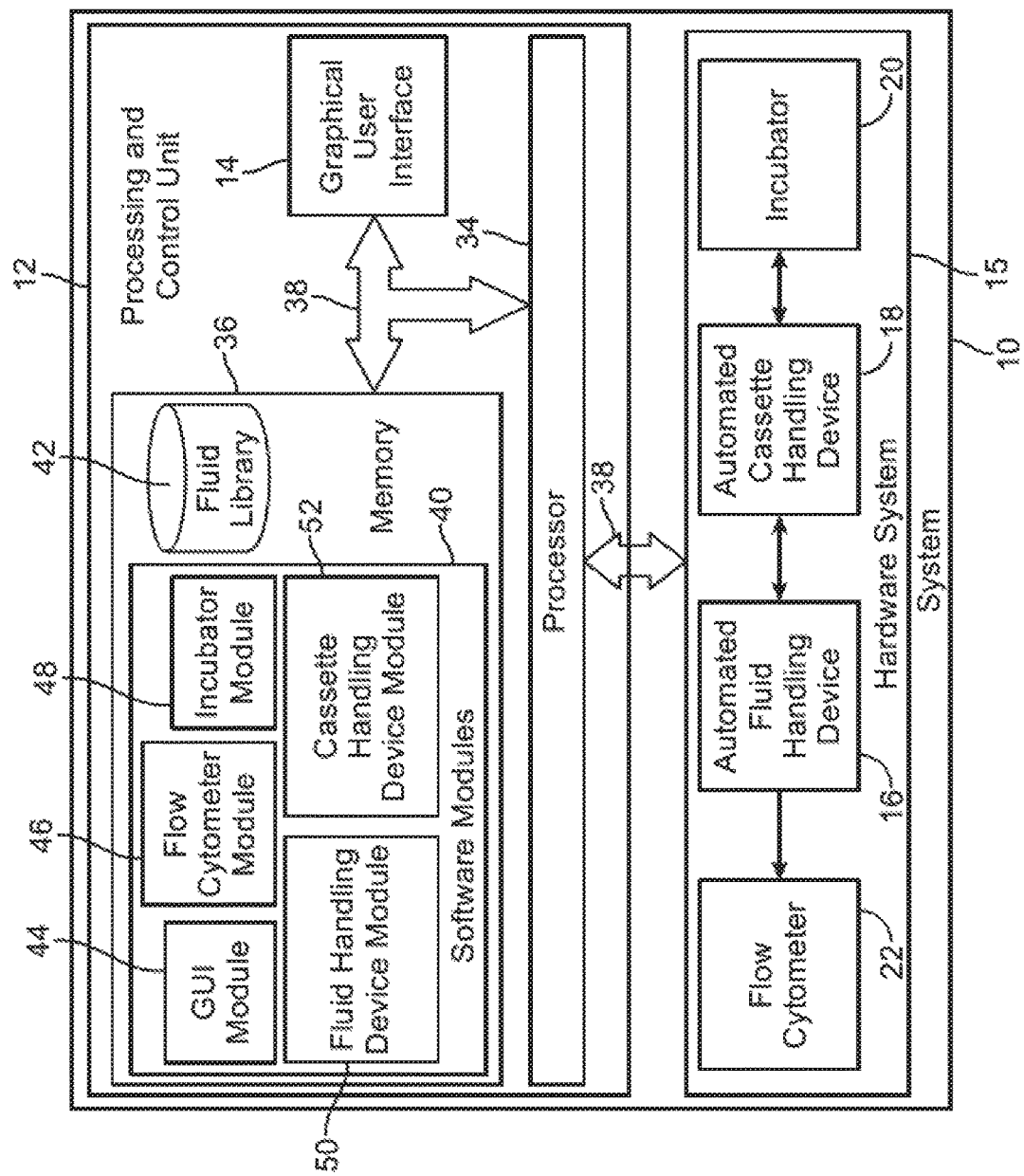
FIG. 1 is a functional block diagram of an automated flow cytometry and fluid handling system made in accordance with the present disclosure.

FIG. 1 illustrates an exemplary embodiment of a flow cytometer and fluid handling system 10, which includes processing and control unit 12 with a graphical user interface (GUI) 14 to allow a user to control operation of system hardware components. Hardware system 15 may include hardware components such as fluid handling system 16, automated cassette handling system 18, incubator 20 and flow cytometer 22. As described more below, flow cytometer 22 performs a variety of measurements on clinical fluid samples, however, it can only analyze one clinical sample at a time. In one example, a multi-well cassette (FIG. 2) may be used to hold multiple samples. Fluid handling system 16, automated cassette handling system 18, and incubator 20 may include one or more robotic components controlled by processors (e.g. processor 34), and may be designed and configured to automatedly transport multi-well cassettes 200 between incubator 20 and flow cytometer 22 and transport clinical samples from a given cassette to the flow cytometer for analysis. Fluid handling system 16 may include, for example, an automated pipetting system, as well as one or more cassette handling robots and microplate washers. Automated cassette handling system 18 may be configured to transport cassettes between fluid handling system 16 and incubator 20. In some examples, automated cassette handling system 18 may be omitted and cassettes may be manually transported between fluid handling system 16 and incubator 20. As will be appreciated, the number of one or more of components in hardware system 15 may vary. For example, one or more of fluid handling system 16, automated cassette handling system 18, and incubator 20 may be configured to function with only one flow cytometer 22, or a plurality of flow cytometers.

Processing and control unit 12 may comprise processor 34 and memory 36. The memory and processor communicate with GUI 14 and hardware system 15 through appropriate application programming interfaces (API) and communication buses 38. Configurations with respect to processor communication and control are described in more detail below with respect to FIG. 5. Components of memory 36 may include software modules 40 configured specifically to control and operate the connected hardware components and fluid library 42. Exemplary software modules may comprise GUI module 44, flow cytometer module 46, incubator module 48, fluid handling device module 50, and cassette handling device module 52. Fluid library 42 is populated with fluid and bacteria specific information used for analyzing the particular type of fluid under analysis, such as, but not limited to, urine, spinal fluid and blood. For example, flow cytometer software module 46 may access pre-defined regions of interest (ROIs), scatter values and fluorescence values etc. stored in the fluid library for detecting various species of bacteria in various fluids being tested. Detections in the ROI possessing characteristics of target events, such as scatter values and fluorescence values, as determined by gating strategies and/or computational analysis executed by the flow cytometer software may be used to determine concentration of particles, cells or bacteria of interest in the sample.

Figure 2:
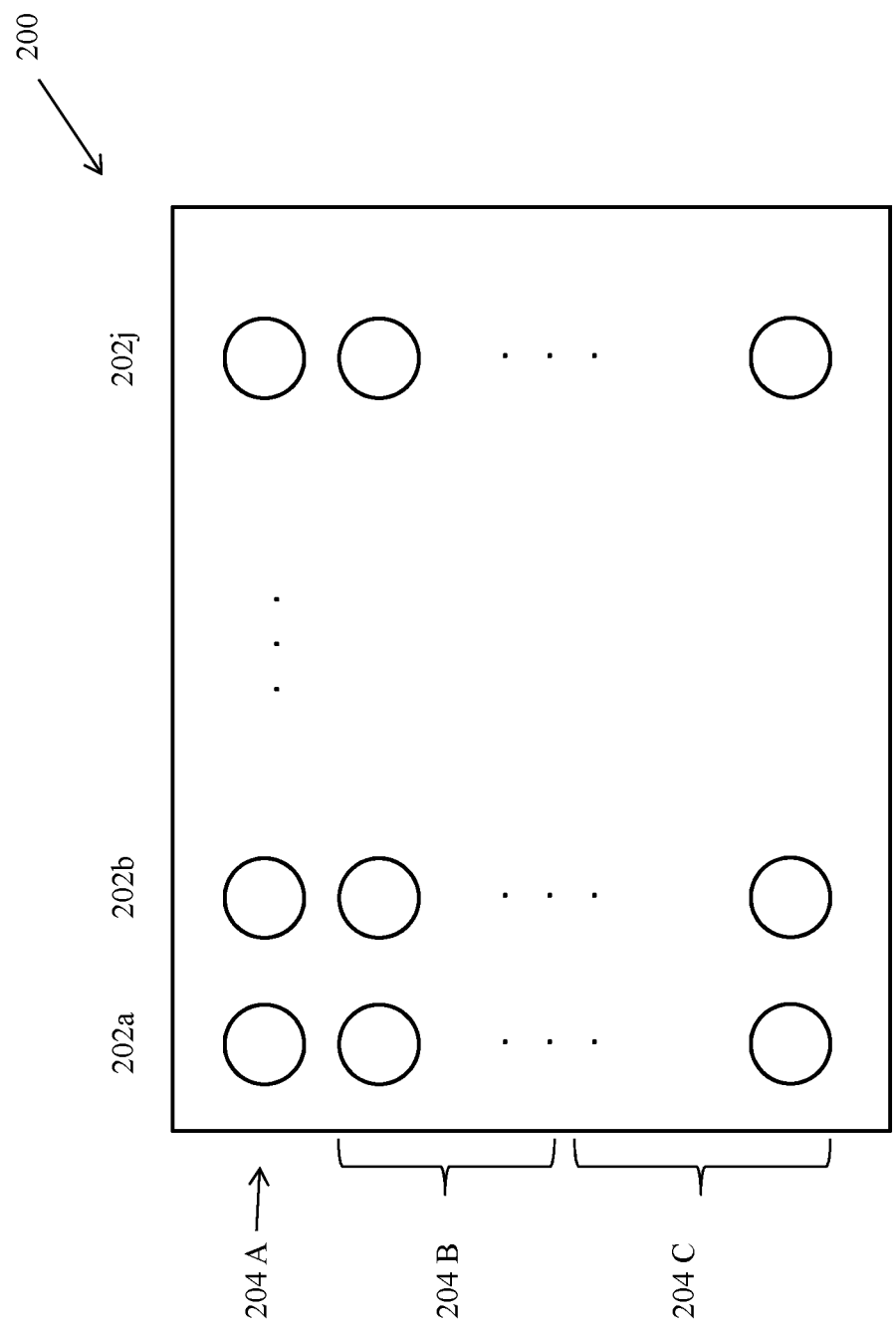
FIG. 2 is an example multi-well cassette that may be used for performing methods of the present disclosure.

FIG. 2 illustrates an example multi-well cassette 200 for holding a plurality of clinical fluid samples for analysis by flow cytometer(s) 22. Cassette 200 includes a plurality of columns 202a-202j of wells, each column including a plurality of wells 204. In this example, "j" is a variable indicating that any number of columns may be used. In one example, separate clinical fluid samples are initially deposited in the first row (wells 204a) of each column 202 and the first row of wells are then used as a reservoir for drawing portions of the fluid sample for further processing and analysis by system 10. For example, if j=6, meaning cassette 200 includes six columns 202, six different fluid samples, e.g., urine samples from, e.g., six different patients, can be loaded into cassette 200 for automated processing.

Figure 3:
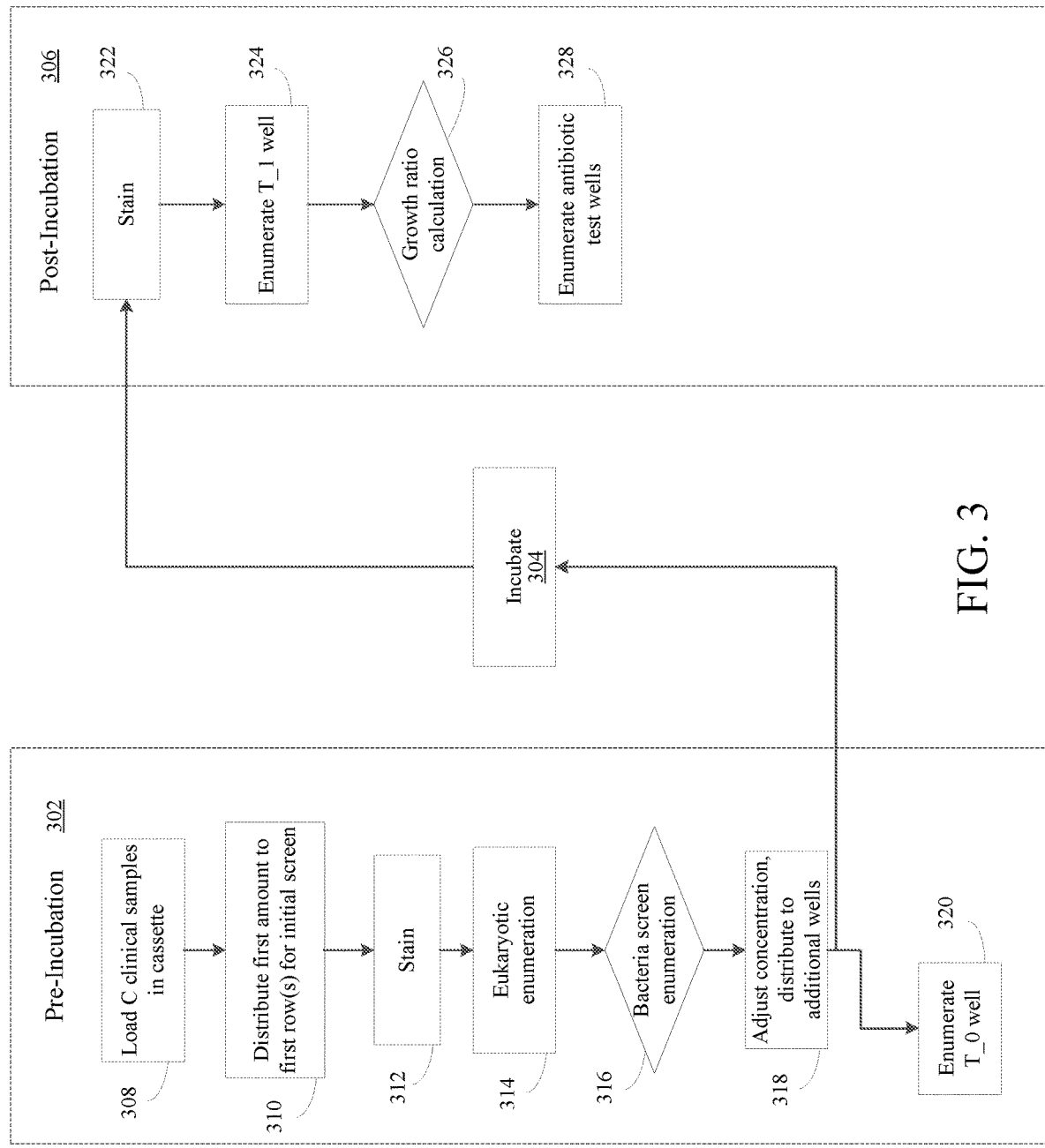
FIG. 3 is an example process for analyzing a multi-well cassette for rapid determination of bacterial infection and antibiotic susceptibility.

FIG. 3 illustrates an example process 300 for analyzing a single multi-well cassette 200 with system 10. In one exemplary embodiment, process 300 includes three phases—a pre-incubation phase 302, where an initial screening analysis is performed on one or more clinical samples to determine, for example, whether one or more samples contain a bacterial infection, an incubation phase 304, where one or more clinical samples are incubated for a specific period of time, and a post-incubation phase 306, where one or more samples are analyzed to verify the sample contains an infection of pathogenic bacteria and to identify one or more antibiotics that may be effective in combating the pathogenic bacteria population(s).

Pre-incubation phase 302 may begin at step 308, with a single volume of a sample being loaded in the first row 204a of cassette 200. For a cassette containing j columns of wells, j samples may be loaded in the first row 204a of corresponding respective columns 202a-j. Cassette 200 may have a predetermined volume of growth media, e.g., 1 ml, in one or more media wells. In one example, Mueller Hinton Broth may be used as the growth media. Fluid handling system 16 may contain one or more wells, volumes, or containers, with dyes, staining agents, control beads, and antibiotics for use during an automated analysis process.

At step 310, after j samples are loaded in row 204a, fluid handling system 16 may utilize automated pipetting system or other suitable probe to remove, e.g., aspirate, a predetermined amount of each sample to row(s) in row group 204b for pre-incubation analysis. In one example, row group 204b include two rows. At step 312, fluid handling system 16 may obtain appropriate cellular stains from designated positions in the fluid handling system and stain the fluid samples in rows 204b. In some embodiments, the dyes may include at least two different dyes, for example one dye that permeates only dead cells, e.g., propidium iodide, and another that permeates all cells, e.g., thyzol orange. Using distinct dye types in this manner allows for discrimination between live and dead cells based on the different fluorescence characteristics of the different dyes when interrogated by appropriate excitation light sources(s).

At step 314, fluid handling system 16 may then deliver the contents of a first well, e.g., a first row 204b of a first column 202a to flow cytometer 22 for a first analysis, e.g., eukaryotic enumeration. The analysis may include scatter plots and fluorescence plots that include gates for red and white blood cell counts. This analysis enables accurate enumeration of specific cell populations that may provide clinically relevant information for the disease process being screened. As an example, the presence of white blood cells in urine samples being screened for urinary tract infections is a secondary indicator of active infection, above and beyond the presence of bacteria.

In one embodiment, next, at step 316, contents of one sample column 202 in a second row in row group 204b are delivered by fluid handling system 16 to flow cytometer 22 for bacteria screen enumeration. Scatter plot gating and fluorescence intensity analysis may again be used to determine a bacteria count corresponding to events falling within an ROI. The bacteria screen count of step 316 may utilize the live/dead cell staining applied at step 312 to exclude dead cells from the bacteria enumeration. The live bacteria cell enumeration can be compared to predetermined threshold values to assess whether continued analysis of the sample is warranted. For example, current clinical standards relative to assessment of urinary tract infections indicate thresholds of $10^4$/ml or $10^5$/ml depending on factors such as clinical status of the patient. Other threshold values may be applied as appropriate for analysis of other clinical indications or other clinical situations.

It should be noted that while the bacteria screen step 316 may be conducted to largely eliminate dead cells from the cell count based on use of fluorescence discriminating dyes, cell count at this stage may still include all types of live cells, both live cells of interest and live cells that are not of interest that may thus be considered as contaminant cells. For example, in assessment of urinary tract infections, a primary pathogenic bacteria of interest is *E. coli*. However, a typical human urine sample may also include many different species of non-pathogenic flora. These non-pathogenic flora may be considered as contaminants with respect to accurate clinical analysis of pathogens.

Thus, after completion of step 316 system 10 may stop analyzing samples in one or more of columns 202. For example, the bacteria count determined at step 316 for one or more of the samples initially loaded in columns 202*a-j* may have a bacteria count below the applicable threshold, indicating the sample does not meet a clinical definition of a bacterial infection and does not require additional processing and analysis.

Based on bacterial count determined in the preceding steps, in step 318 sample concentration is adjusted to a target bacterial level and samples distributed from row 204*a* to row group 204*c* for further analysis. In one example, this step is omitted for any sample(s) that system 10 determined at step 316 did not contain a live bacteria count above the applicable threshold. As is known in the art, testing of bacteria for antibiotic resistance or susceptibility typically requires a bacterial concentration in the range of approximately $1\times10^5$ to approximately $1\times10^6$ bacteria/ml. However, depending on the sensitivity and accuracy of the instrumentation employed (for example some flow cytometer systems are more sensitive than others), lower concentrations may be employed. Thus, methods of the present disclosure may be employed with concentrations as low as in the range of $1\times10^3$ bacteria/ml. For example, instrument sensitivity may indicate a concentration in the range of approximately $1\times10^4$ bacteria/ml to approximately $5\times10^4$ bacteria/ml, or other instrumentation may employ a concentration in the range of approximately $1\times10^3$ bacteria/ml to approximately $5\times10^3$ bacteria/ml. Various antimicrobial efficacy testing methods may require a standard concentration of bacteria, e.g., a predetermined bacterial concentration of $1\times10^5$ bacteria/ml.

Adjustment of sample concentration at step 318 can be accomplished by addition of appropriate amounts of growth media when samples are further distributed by fluid handling system 16. If initial testing of a clinical sample indicates a higher concentration, e.g., if the flow cytometer enumerates an initial sample at 1×107 bacteria/ml, the system may automatically adjust the concentration for subsequent testing. In one example, I microliter of the sample may be aspirated by the fluid handling system and deposited into I 000 microliters of media in a first one of media wells 204*c* to arrive at the target concentration of 1×104. In another example, the initial concentration may be greater than 1×107bacteria/ml, and/or the minimum aspiration volume may be greater than I microliter, and/or the target concentration may be lower, etc. such that a second dilution step is required. The fluid handling system may be configured to determine a second amount of fluid to be aspirated from the first media well containing media and the first amount of the fluid sample for deposit in a second media well in group 204*c* to arrive at the target concentration, e.g., 1×104bacteria/ml.

Sample distribution at step 318 includes distribution of a time zero control, T0, sample to a first well in group 204*c* as well as a T1 sample to a second well in group 204*c*. Optionally further samples may be distributed to antibiotic testing (AT) well(s) in group 204*c*. In one embodiment, adjustment step 318 is accomplished by depositing a properly diluted sample in an initial well in group 204*c* and then distributing an amount of the properly-diluted sample from the initial well to all other wells to be employed.

At step 320, a first sample, referred to herein as a T0 sample, from the properly-diluted samples in group 204*c*, is transported to flow cytometer 22 to obtain a baseline time-zero bacteria count. After removing a portion of the T0 sample from cassette 200 for enumeration, at step 304 the cassette 200 containing a second sample for enumeration after incubation, the T1 sample, and any desired antibiotic testing samples is delivered to incubator 20 by automated cassette handling system 18 and incubated. AT wells in group 204*c* may be prefilled with specific antibiotics against which testing is to be run or may be separately filled from an appropriate source by the fluid handling system. Incubation time will depend on the nature of the cells to be studied. For example, with respect to cells of interest, such as urogenital flora, incubation time may be in the range of about 2.5 hours, or typically less than about 3 hours, but more than 2 hours. As described more below, in some examples, it can be very important that each cassette 200 containing the same type of fluid sample is incubated for the same period of time.

After incubation, at step 322, the multi-well cassette is returned to fluid handling system 16 by automated cassette handling system 18. At step 322, all T1 samples and AT wells in group 204*c* are stained by fluid handling system 16. In one example, the same live/dead stains that were used in step 312 are used here. Thereafter, at step 324 T1 samples are enumerated and the growth ratio after incubation, i.e., ratio of T1 to T0 cells, is determined at step 326.

Enumeration (316, 324) and assessment of the T1/T0 cell growth ratio (326) are important steps to allow quantitative discrimination between pathogenic cells/bacteria of interest and contaminant cells/bacteria. It has been determined by the Applicant that pathogenic bacteria exhibit different growth rates as compared to non-pathogenic, contaminant bacteria and that these differences in growth rate may be used to discriminate qualitatively between cells of clinical interest and contaminant cells, without reliance on more subjective measures such as species identification using chemical means or matrix assisted laser desorption/ionization time of flight mass spectrometry (MALDI-ToF). For example, it has been determined that pathogenic cells in human urine exhibit a growth rate that is approximately 5×±1 greater than the growth rate of contaminant cells when cultured over short culture times in the range of approximately 2.5 hours. It may be possible in certain circumstances to state the growth rate difference more specifically as 5×±0.5. Thus in one embodiment, if the $T_1$ to $T_0$ cell growth ratio is determined to be between about 6.25× and 16.25× (i.e., about 125% to about 325%) the sample may be assessed as a positive for pathogenic bacteria.

In another embodiment, the system may be programed to convert the relative growth between $T_0$ and $T_1$ to an integer representing bacterial population expansion. In such an embodiment, the derived growth integer from T0 baseline to T1 control growth is compared to the known growth integers of a known library of pathogens represented in the disease state being tested. Representative disease states may include, but are not limited to, pathogens associated with urinary tract infections, pathogens associated with blood stream infections (bacteremia/sepsis), pathogens associated with meningitis or other neurologic infections. Alternatively or additionally, the derived growth integer is compared to the known growth integers of a known library of possible bacterial contaminants represented in the disease state being assessed, such as, but not limited to normal urogenital flora associated with suspected urinary tract infections or possible skin contaminant associated with blood sampling in suspected bacteremia samples. Known libraries of pathogens and contaminants may be stored in fluid library 42 in memory 36.

Depending on the clinical objective, for example if simply determining existence of a urinary tract infection is the goal, then the positive result may be the stopping point and the result reported to the appropriate health care provider or patient. However, embodiments of the present disclosure also provide for rapid assessment of antibiotic resistance/susceptibility prediction if such information is desired. If the result of the assessment in step 326 is positive, enumeration of the samples placed in the AT wells may proceed. Because the samples were distributed to the AT wells at the same time as the T0 and T1 wells, the samples in the AT wells were cultured also during incubation step 304 and thus may be immediately enumerated without additional culture time. At step 328, samples from AT wells in group 204c for each of columns 202 that tested positive at steps 316 and 326 are enumerated to determine an antibiotic prediction profile or for use as information in determining antibiotic susceptibility based on comparison with the T1 sample. For these comparisons, the T1 enumeration provides a baseline against which the AT well enumeration is compared. Resistance prediction may be based on growth rate thresholds as may be established for specific clinical indications and/or drugs and antibiotics. Note that once again, by using flow cytometer enumeration and comparing the ratio of, e.g., ATn/T1, a quantitative measurement of the antibiotic/drug effectiveness may be determined.

Automated flow cytometry systems made in accordance with the present disclosure can be configured to process a plurality of multi-well cassettes, such as multi-well cassette 200, each of which may contain a plurality of different fluid samples. As described above in connection with FIG. 3, the analysis of each cassette includes three phases—a pre-incubation phase 302, an incubation phase 304, and a post-incubation phase 306. After system 10 performs pre-incubation phase 302 on a first cassette and the first cassette is deposited in incubator 20, the first cassette will need to remain in the incubator for a relatively long time, e.g., three hours. System 10 can, therefore, begin the pre-incubation phase 302 for a second cassette, however, as noted above, it is important that post-incubation phase 306 begins substantially immediately after reaching the required incubation time because the growth ratio calculations performed at steps 326 and 328 and determinations of infection and antibiotic effectiveness are based on a pre-determined incubation time and temperature.

Figure 4:
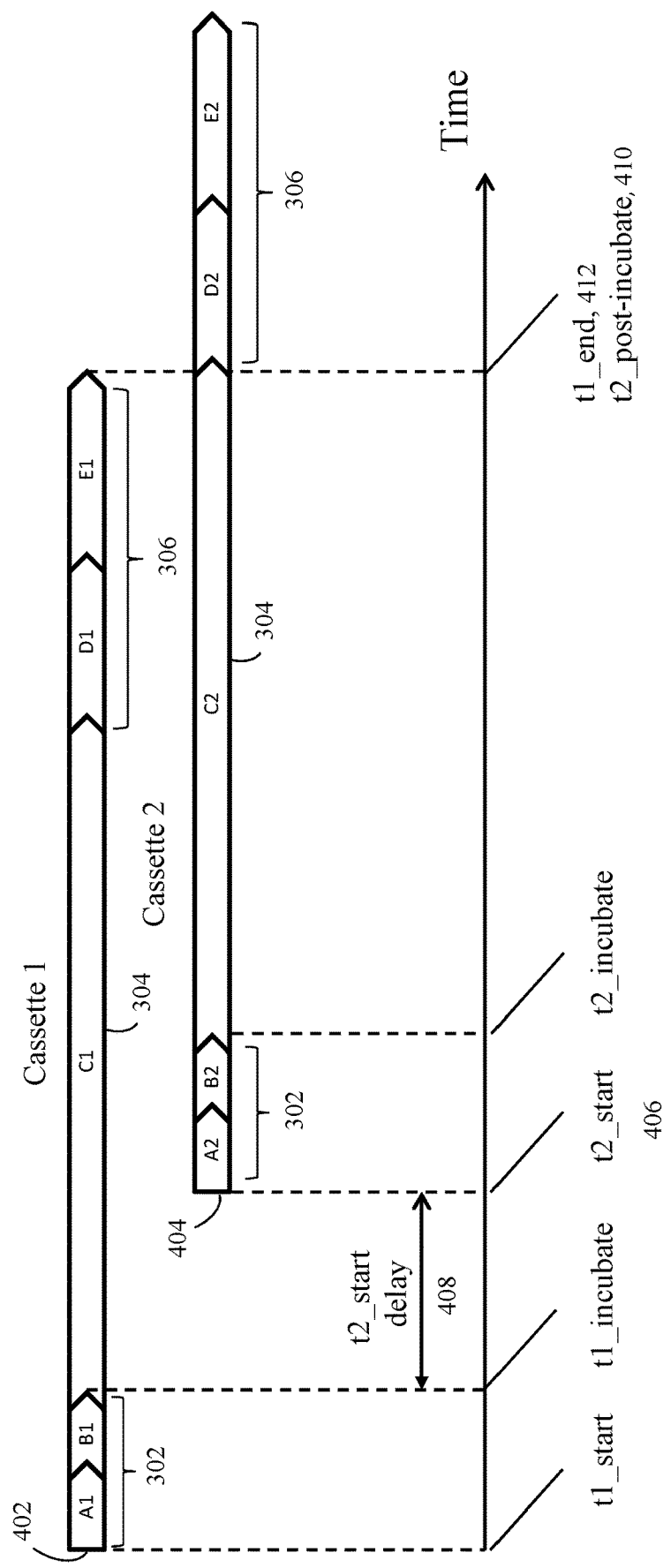
FIG. 4 is an example timeline for sequentially processing a plurality of multi-well cassettes, each cassette containing a plurality of clinical fluid samples.

This time dependency between the analysis of sequential cassettes is illustrated in FIG. 4, which shows a timeline 402 for analysis of a first cassette and a timeline 404 for analysis of a second cassette. Pre-incubation phase 302 includes a first period A that represents a portion of the pre-incubation phase through an initial live bacteria enumeration, e.g., steps 308-316. Second period B, which is the amount of time required to perform a pre-incubation process on x clinical samples of a cassette after an initial live bacteria enumeration, e.g., steps 318-320. As noted above, after the initial bacteria screen at step 316, system 10 may be configured to only continue to process the samples that have a live bacteria count that exceeds a pre-determined threshold, such that time period B of pre-incubation phase 302 may vary from cassette to cassette.

Timelines 402, 404 also include the incubation phase C1 304, and contain post-incubation phase 306, which include a first period, D, which represents the amount of time after incubation through performing a growth ratio determination process, e.g., steps 322-326. Post-incubation phase 306 may also include a second period, E, which is the amount of time required to perform a bacteria susceptibility determination process, e.g., step 328. As noted above, in some examples, system 10 may be configured to only perform step 328 to analyze the AT wells for samples that meet or exceed a threshold ratio determined in step 326.

As shown conceptually in FIG. 4, system 10 may need to delay the start of the second cassette, t2_start 406 by a delay time t2_start delay 408 to ensure the beginning of post-incubation phase 306 for cassette 2 (t2_post-incubate 410) does not occur prior to the end of post-incubation phase 306 for cassette 1 (t1_end 412). Incorporating any required delay prior to analysis of cassette 2 ensures flow cytometer 22 has completed the post-incubation phase 306 for a first cassette and is available to begin the post-incubation phase 306 of a second cassette. As noted above, this can be important for ensuring the accuracy and reliability of the measurements and analytical results for the second cassette. As will be appreciated, FIG. 4 is a simplified conceptual illustration of only two cassettes, however, system 10 can be configured to concurrently process a significantly greater number of multi-well cassettes, with a plurality of the cassettes undergoing incubation phase 304 in incubator 20 at the same time. The relationship illustrated in FIG. 4 applies to any two sequential cassettes. Also, the relative durations of the phases illustrated in FIG. 4 are not drawn to scale. For example, incubation phase 304 may be a longer duration relative to pre and post incubation 302, 306. Also, as noted above, at least time periods B, D, and E may vary from cassette to cassette, depending on the number of clinical samples that test positive for a bacterial infection.

Figure 5:
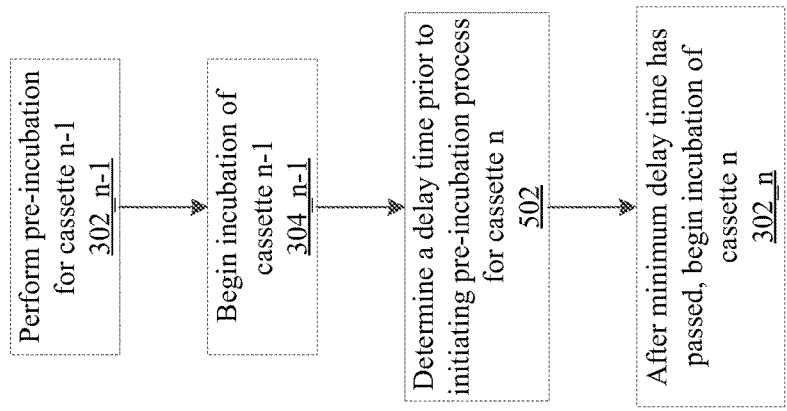
FIG. 5 is a flow chart illustrating a method of performing a sequential automated flow cytometry process on a plurality of multi-well cassettes.

FIG. 5 illustrates a method of sequentially performing the automated flow cytometry process of FIG. 3 on two multi-well cassettes. As shown in FIG. 5, at step 302_n-1 the pre-incubation process steps 302 (FIG. 3) are performed on a first cassette n-1. At step 304_n-1, the incubation of first cassette n-1 begins, and at step 502, a delay time prior to initiating the pre-incubation process 302 for a subsequent cassette n is determined. At step 302_n, after the required delay time after incubation of cassette n-1 has passed, the pre-incubation process 302_n for cassette n begins.

Processor 34 may be configured to execute one or more calculations in connection with performing step 502 of FIG. 5—determination of a delay time, as well as other delay times as described below. In one example, calculations for determining a delay in a start time for analysis of a given multi-well cassette, n, may involve one or more of Equations (1)-(6) as follows:

$$t_{delay_n} > t_{post\text{-}incubation,n-1} - t_{pre\text{-}incubation,n} \qquad \text{Eq. (1)}$$

wherein:

$t_{delay_n}$ is the minimum required time delay prior to beginning a first step, e.g., step 308 of an automated flow cytometry process of a cassette, n, after an incubation period of a previously-analyzed cassette, n-1, begins;

$t_{post\text{-}incubation,n-1}$ is the amount of time required to complete post incubation processes, e.g., steps 322-328, after an incubation, e.g., step 304 of previously analyzed cassette, n-1; and $t_{pre\text{-}incubation,n}$ is the amount of time required to complete pre-incubation processes, e.g., steps 308-320.

$$t_{post\text{-}incubation,n-1}(x,y) = t_{D,n-1}(x) + t_{E,n-1}(y) \qquad \text{Eq. (2)}$$

wherein:

$t_{D,n-1}(x)$ is the amount of time required to perform a growth ratio determination process, e.g., steps 322-326; and $t_{E,n-1}(y)$ is the amount of time required to perform a bacteria susceptibility determination process, e.g., step 328.

$$t_{D,n-1}(x) = j + k*x \qquad \text{Eq. (3)}$$

wherein:
 j is a constant, in some examples, about 5 to 15 minutes, and in some examples, about 12 minutes;
 k is a constant, in some examples, about 1 to 3 minutes, and in some examples about 1.25 minutes; and
 x is the number of clinical samples containing a concentration of live bacteria above a threshold value, determined during a pre-incubation live bacteria enumeration process, e.g., step 316.

$$t_{E,n-1}(y) = l + m*y \qquad \text{Eq. (4)}$$

wherein:
 l is a constant, in some examples, about 5 to 10 minutes, and in some examples, about 8 minutes;
 m is a constant, in some examples, about 5 to 10 minutes, and in some examples about 7 minutes; and
 y is the number of clinical samples containing bacteria population(s) having a rate of bacteria population expansion during an incubation period that exceeds a threshold value, determined during a post-incubation live bacteria enumeration process and comparison to a pre-incubation bacteria enumeration, e.g., step 326.

$$t_{pre-incubation,n}(c,x) = t_{A,n}(c) + t_{B,n}(x) \qquad \text{Eq. (5)}$$

wherein:
 $t_{A,n}(c)$ is the amount of time required to perform a pre-incubation process through an initial live bacteria enumeration, e.g., steps 308-316;
 $t_{B,n}(x)$ is the amount of time required to perform a pre-incubation process on x clinical samples of a cassette after an initial live bacteria enumeration, e.g., steps 318-320;
 c is the number of clinical samples that can be loaded on a cassette; and
 x is the number of clinical samples containing a concentration of live bacteria above a threshold value, determined during a pre-incubation live bacteria enumeration process, e.g., step 316.

$$t_{B,n}(x) = n + o*x \qquad \text{Eq. (6)}$$

wherein:
 n is a constant, in some examples, about 11 to 20 minutes, and in some examples, about 35 minutes;
 o is a constant, in some examples, about 13 to 30 minutes, and in some examples, about 50 minutes; and
 x is the number of clinical samples containing a concentration of live bacteria above a threshold value, determined during a pre-incubation live bacteria enumeration process, e.g., step 316.

Thus, as described above, the minimum required time delay before commencing pre-incubation phase 302 is a function of the duration of the pre-incubation phase for that cassette and the post-incubation phase 306 for the previously-analyzed cassette. As noted above, the time duration of the post-incubation phase is a function of the number of clinical samples contained on the cassette that tested positive in the initial screening step 316, and the number of samples that tested positive in the growth ratio calculation step 326 (FIG. 3). Thus, the minimum required time delay for cassette n increases as the number of clinical samples on cassette n-1 containing a bacterial infection increase. As will be appreciated, Equation (1) represents a minimum time delay and a longer time delay prior to commencement of analysis of a subsequent cassette may be used. Further, the example described above assumes a constant incubation time for all cassettes, however, Equations 1-6 can be readily modified to incorporate a variable incubation time, which may be applicable when cassettes with differing types of fluids, e.g., urine, blood, and/or cerebral spinal fluid, are being analyzed by system 10 at the same time. In another example, system 10 may incorporate two time delays. For example, the initial time delay $t_{delay_n}$ may assume a nominal number of samples on cassette 200 will test positive in screening step 316. As illustrated in Equations 1, 5, and 6, if the assumption over-predicts the number of infected samples, the time duration of the pre-incubation phase will be shorter, requiring a longer minimum time delay $t_{delay_n}$. A second time delay may be incorporated prior to commencing with step 318 to account for the over-prediction to ensure cassette n does not begin incubation too soon.

As will be appreciated, one or more of software modules 40 may include machine executable instructions, executable by processor 34, for automatically determining any required time delays prior to processing a multi-well cassette, which may involve accessing the results from one or more of steps 316, 324 and 326, which may be stored in memory 36 and for otherwise coordinating the parallel processing of a plurality of multi-well cassettes 200 with one or more flow cytometers 22.

Any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
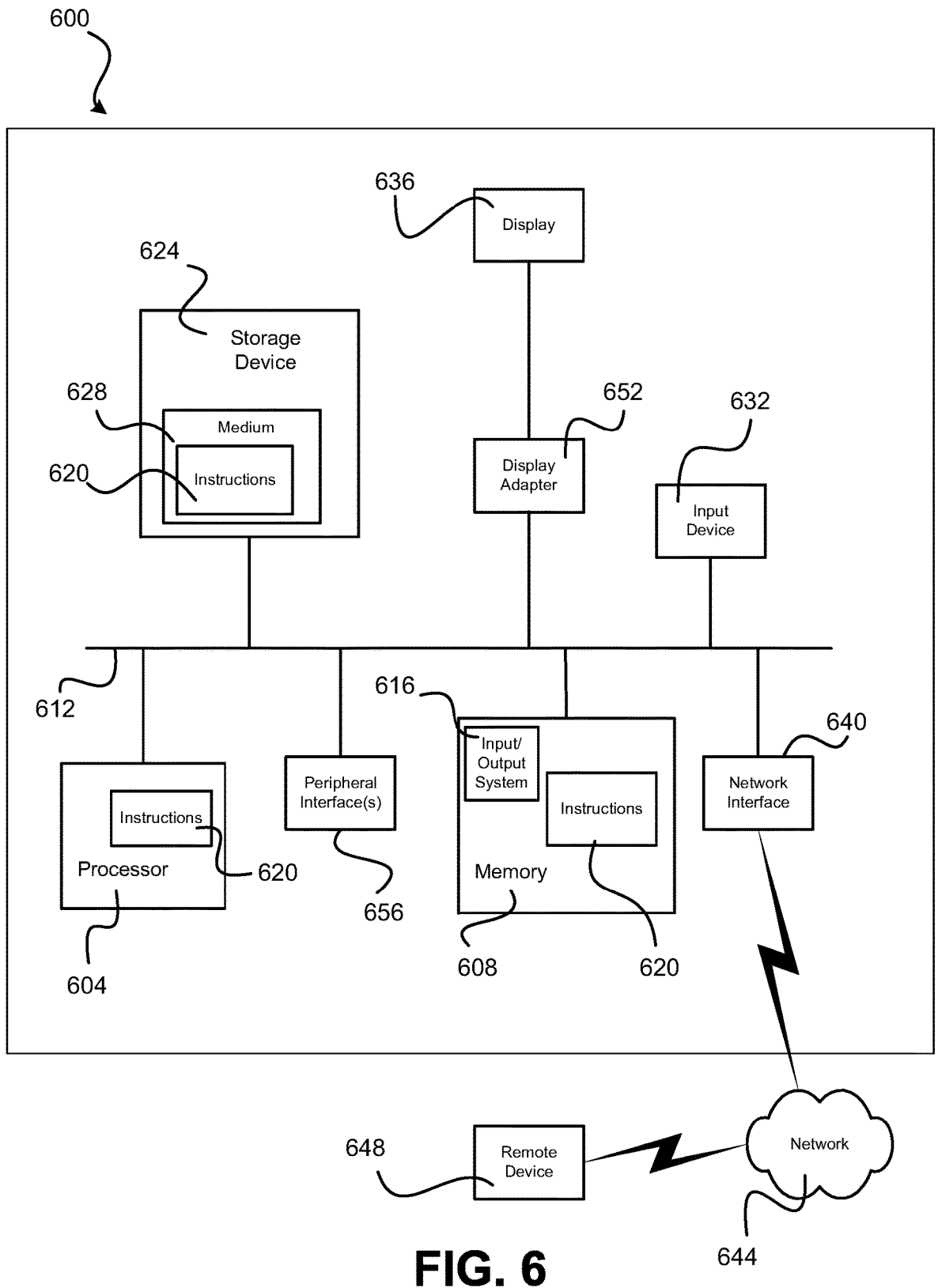
FIG. 6 is a functional block diagram of an example control system that may be used to implement aspects of the present disclosure.

FIG. 6 shows a diagrammatic representation of one embodiment of a computing device in the exemplary form of a computer system 600 within which a set of instructions for causing a control system, such as the automated flow cytometry system of FIG. 1, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of sequencing an analysis of multi-well cassettes each containing a plurality of fluid samples, the method comprising:
   automatically pipetting, through a fluid handling system, a first multi-well cassette containing a first plurality of fluid samples;
   performing a pre-incubation analysis of the first plurality of fluid samples of the first multi-well cassette through the fluid handling system, wherein the pre-incubation analysis includes determining a concentration of live bacteria through bacteria enumeration;
   receiving, from the fluid handling system, pre-incubation analysis results for the first multi-well cassette containing the first plurality of fluid samples, wherein the pre-incubation analysis results indicate a number of the first plurality of fluid samples that contain a concentration of live bacteria above a threshold value;
   determining, according to the pre-incubation analysis results, a duration of time for performing a post-incubation analysis of one or more of the first plurality of fluid samples with a flow cytometer;
   determining at least one of a start time for a pre-incubation analysis of a second multi-well cassette with the flow cytometer, or a start time of an incubation period for the second multi-well cassette, according to the determined duration of time for performing the post-incubation analysis.

2. The method of claim 1, further comprising:
   receiving a value for a number of a second plurality of fluid samples loaded on the second multi-well cassette; and
   determining, according to the received value, a duration of time to perform the pre-incubation analysis of the second plurality of fluid samples with the flow cytometer, wherein the pre-incubation analysis includes a determination of an initial live bacteria enumeration in each of the second plurality of fluid samples;
   wherein the step of determining at least one of the start time for the pre-incubation analysis of the second multi-well cassette or the start time of the incubation phase for the second multi-well cassette further includes determining the at least one of the start times according to the determined duration of time to perform the pre-incubation analysis of the second plurality of fluid samples.

3. The method of claim 1, further comprising, receiving a required incubation time duration for the first plurality of fluid samples, wherein the step of determining the at least one of the start times includes determining at least one of the start times according to the received required incubation time.

4. The method of claim 1, further comprising:
   receiving post-incubation analysis results for the first multi-well cassette, wherein the post-incubation analysis results indicate a number of fluid samples in the first multi-well cassette that contain bacteria population having a rate of bacteria population expansion during an incubation period that exceeds a threshold value;
   wherein the step of determining at least one of the start times includes determining at least one of the start times according to the received post-incubation analysis results.

5. The method of claim 4, wherein the post-incubation analysis results are determined during a flow cytometer post-incubation live bacteria enumeration process that includes a comparison to the pre-incubation analysis results of the first multi-well cassette.

6. The method of claim 1, wherein the pre-incubation analysis results are based on flow cytometer testing of the first plurality of fluid samples in the first multi-well cassette during a pre-incubation live bacteria enumeration testing process.

7. The method of claim 1, wherein the fluid samples are urine, blood, or cerebral spinal fluid.

8. A non-transitory machine-readable storage medium containing machine-readable instructions configured to cause a processor of a flow cytometer and fluid handling system to perform operations comprising:
   automatically pipetting, through a fluid handling system, a first multi-well cassette containing a first plurality of fluid samples;
   performing a pre-incubation analysis of the first plurality of fluid samples of the first multi-well cassette through the fluid handling system, wherein the pre-incubation analysis includes determining a concentration of live bacteria through bacteria enumeration;
   receiving, from the fluid handling system, pre-incubation analysis results for the first multi-well cassette containing the first plurality of fluid samples, wherein the pre-incubation analysis results indicate a number of the first plurality of fluid samples that contain a concentration of live bacteria above a threshold value;
   determining, according to the pre-incubation analysis results, a duration of time for performing a post-incubation analysis of one or more of the first plurality of fluid samples with a flow cytometer; and determining at least one of a start time for a pre-incubation analysis of a second multi-well cassette with the flow cytometer, or a start time of an incubation period for the second multi-well cassette, according to the determined duration of time for performing the post-incubation analysis.

9. The non-transitory machine-readable storage medium according to claim 8, wherein the operations further comprise:

receiving a value for a number of a second plurality of fluid samples loaded on the second multi-well cassette; and determining, according to the received value, a duration of time to perform the pre-incubation analysis of the second plurality of fluid samples with the flow cytometer, wherein the pre-incubation analysis includes a determination of an initial live bacteria enumeration in each of the second plurality of fluid samples;

wherein the step of determining at least one of the start time for the pre-incubation analysis of the second multi-well cassette or the start time of the incubation phase for the second multi-well cassette further includes determining the at least one of the start times according to the determined duration of time to perform the pre-incubation analysis of the second plurality of fluid samples.

10. The non-transitory machine-readable storage medium according to claim 8, wherein the operations further comprise receiving a required incubation time duration for the first plurality of fluid samples, wherein the step of determining at least one of the start times includes determining at least one of the start times according to the received required incubation time.

11. The non-transitory machine-readable storage medium according to claim 8, wherein the operations further comprise:

receiving post-incubation analysis results for the first multi-well cassette, wherein the post-incubation analysis results indicate a number of fluid samples in the first multi-well cassette that contain bacteria population having a rate of bacteria population expansion during an incubation period that exceeds a threshold value;

wherein the step of determining at least one of the start times includes determining at least one of the start times according to the received post-incubation analysis results.

* * * * *